United States Patent
Fuchs et al.

(10) Patent No.: US 11,000,245 B2
(45) Date of Patent: May 11, 2021

(54) COMPACT TUNABLE X-RAY SOURCE BASED ON LASER-PLASMA DRIVEN BETATRON EMISSION

(71) Applicant: NUtech Ventures, Lincoln, NE (US)

(72) Inventors: Matthias Fuchs, Lincoln, NE (US); Ping Zhang, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 16/565,147

(22) Filed: Sep. 9, 2019

(65) Prior Publication Data

US 2020/0085388 A1 Mar. 19, 2020

Related U.S. Application Data

(60) Provisional application No. 62/728,324, filed on Sep. 7, 2018.

(51) Int. Cl.
| | |
|---|---|
| *H05G 2/00* | (2006.01) |
| *A61B 6/00* | (2006.01) |
| *H01J 35/22* | (2006.01) |

(52) U.S. Cl.
CPC .............. *A61B 6/40* (2013.01); *H01J 35/22* (2013.01)

(58) Field of Classification Search
CPC .......... A61B 6/40; A61B 6/4064; H01J 35/22; H01J 37/08; H01J 37/00; H05G 2/00; H05G 2/03

See application file for complete search history.

(56) References Cited

U.S. PATENT DOCUMENTS

2016/0014874 A1* 1/2016 Kaganovich ........... H05G 2/008
378/119

OTHER PUBLICATIONS

K. Ta Phuoc et al., "Betatron radiation from density tailored plasmas," Physics of Plasmas 15, 063102 (2008), Jun. 9, 2008.

Corde et al., "Femtosecond x rays from laser-plasma accelerators," Reviews of Modern Physics, vol. 85, No. 1, Jan.-Mar. 2013, published Jan. 9, 2013.

Ta Phuoc et al., "Betatron radiation from density tailored plasmas," Phys. Plasmas 15, 063102 (2008); https://doi.org/10.1063/1.2918657, published Jun. 9, 2008.

Albert et al., "Observation of Betatron X-Ray Radiation in a Self-Modulated Laser Wakefield Accelerator Driven with Picosecond Laser Pulses," PRL 118, 134801 (2017), published Mar. 31, 2017.

Kostyukov et al., "Phenomenological theory of laser-plasma interaction in "bubble" regime," Physics of Plasmas 11, 5256 (2004); https://doi.org/10.1063/1.1799371, published Oct. 22, 2004.

Cipiccia et al., "Gamma-rays from harmonically resonant betatron oscillations in a plasma wake," Nature Physics, vol. 7, Macmillan Publishers Limited, DOI: 10.1038/NPHYS2090, published Sep. 18, 2011.

(Continued)

*Primary Examiner* — Don K Wong
(74) *Attorney, Agent, or Firm* — Leydig, Voit & Mayer, Ltd.; Gerald T. Gray (57) ABSTRACT

Systems and methods for generating tunable x-ray emissions including a tunable x-ray source that includes a driver, such as a laser, configured to generate one or more driver pulses, such as one or more laser pulses, and a target source configured to emit a target material. The target source is arranged so that the emitted target material intersects a propagation axis of the driver pulse(s) and the target source may be configured so that the emitted target material has a tailored density profile along the propagation axis of the driver pulse(s), the tailored density profile along the propagation axis having a first density peak region followed by a lower density region followed by a second density peak region, e.g., in an "M" shape.

16 Claims, 7 Drawing Sheets

(56) References Cited

OTHER PUBLICATIONS

Oz et al., "Ionization-Induced Electron Trapping in Ultrarelativistic Plasma Wakes," Physical Review Letters 98, 084801 (2007), published Feb. 23, 2007.

Esarey et al., "Synchrotron radiation from electron beams in plasma-focusing channels," Physical Review E, vol. 65, 056505, published May 20, 2002.

Chen et al., "Bright betatron X-ray radiation from a laser-driven-clustering gas target," Scientific Reports, 3:1912, DOI:10.1038/srep01912, published May 29, 2013.

Geddes et al., "Plasma-Density-Gradient Injection of Low Absolute-Momentum-Spread Electron Bunches," PRL 100, 215004 (2008), published May 30, 2008.

Popp et al., "All-Optical Steering of Laser-Wakefield-Accelerated Electron Beams," PRL 105, 215001 (2010), published Nov. 16, 2010.

Rowlands-Rees et al., "Laser-Driven Acceleration of Electrons in a Partially Ionized Plasma Channel," PRL 100, 105005 (2008), published Mar. 14, 2008.

Pukhov et al., "Laser wake field acceleration: the highly non-linear broken-wave regime," Appl. Phys. B 74, 355-361 (2002), published Mar. 14, 2002.

Esarey et al., "Physics of laser-driven plasma-based electron accelerators," Reviews of Modern Physics, vol. 81, Jul.-Sep. 2009, published Aug. 27, 2009.

Faure et al., "Controlled injection and acceleration of electrons in plasma wakefields by colliding laser pulses," Nature Letters, vol. 444, doi:10.1038/nature05393, Nature Publishing Group, Dec. 7, 2006.

Rosenzweig et al., "Acceleration and focusing of electrons in two-dimensional nonlinear plasma wake fields," Physical Review A, vol. 44, No. 10, Nov. 15, 1991.

* cited by examiner

COMPACT TUNABLE X-RAY SOURCE BASED ON LASER-PLASMA DRIVEN BETATRON EMISSION

CROSS-REFERENCE TO RELATED APPLICATIONS

This patent application claims priority to U.S. Provisional Patent Application No. 62/728,324 by Fuchs et al., entitled "COMPACT TUNABLE X-RAY SOURCE BASED ON LASER-PLASMA DRIVEN BETATRON EMISSION," filed Sep. 7, 2018, which is incorporated herein by reference in its entirety.

FEDERALLY SPONSORED RESEARCH OR DEVELOPMENT

This invention was made with Government support IIA1430519 awarded by the National Science Foundation and under FA9550-15-1-0125 awarded by the Air Force Office of Scientific Research. The Government has certain rights in the invention.

SUMMARY

The present disclosure generally provides systems and methods for generating tunable x-ray emissions, and more particularly to generating and controlling ultrashort x-ray pulses via betatron emission from relativistic electron bunches transversely oscillating in a plasma accelerator structure.

According to an embodiment, a tunable x-ray source is provided that includes a driver configured to generate one or more driver pulses, and a target source configured to emit a target material. The target material may be ionized. The target source is arranged so that the emitted target material intersects a propagation axis of the driver pulse(s) and the target source is configured so that the emitted target material has a tailored density profile along the propagation axis of the driver pulse(s), the tailored density profile along the propagation axis having a first density peak region followed by a lower density region followed by a second density peak region. In some embodiments, the tailored density profile may include more than two density peaks, each of which may be separated by a lower density region. Interaction of a driver pulse with the ionized target material along the propagation axis results in betatron emissions in an x-ray wavelength range. In certain aspects, the betatron emissions include x-ray pulses propagating along the propagation direction of the driver with an angular spread relative to the propagation axis. The density peaks each have a higher density than an adjacent lower density region. For example, the first density peak and the second density peak may each have a higher density than the lower density region in between. In certain aspects, the tailored density profile may have an "M" type shape (i.e., as viewed such that the propagation axis intersects the left part or peak of the "M" and travels through middle section of the "M" and out of the right peak of the "M"). In certain aspects, the target source includes a nozzle including two or more exit apertures. In certain aspects, the target material includes a plasma or ionized gas. In certain aspects, the driver includes a laser, e.g., a pulsed laser, an electron beam source that generates an electron beam, or other source capable of generating pulses having a controllable pulse duration on the order of 1 to 5 femtosecond (fs) or less to 50 fs or 100 fs or greater.

According to another embodiment, a method of generating tunable x-ray emissions is provided. The method includes generating a driver pulse that propagates along a propagation axis, and generating a target material, the (generated) target material having a tailored density profile along the propagation axis, the tailored density profile along the propagation axis having at least a first density peak followed by a lower density region followed by a second density peak, wherein interaction of the driver pulse with the target material results in betatron emissions in an x-ray wavelength range. In certain aspects, the betatron emissions include x-ray pulses propagating along the propagation direction of the driver pulse with an angular spread relative to the propagation axis. The first density peak and the second density peak each have a higher density than the lower density region. In certain aspects, the tailored density profile may have an "M" type shape (i.e., as viewed such that the propagation axis intersects the left part or peak of the "M" and travels through middle section of the "M" and out of the right peak of the "M"). In certain aspects, the target material includes a plasma or ionized gas. In certain aspects, the driver pulse has a controllable pulse duration on the order of 1 to 5 femtosecond (fs) or less to 50 fs or 100 fs or greater.

In certain aspects, each driver pulse (e.g., laser pulse or electron beam pulse) has a power of from about 1 TW to about 1 PW or more or a beam current from about 100 A to about 10 kA or more. In certain aspects, the betatron emissions has a photon energy of from about 0.5 keV or less to about 100 keV or more. In certain aspects, the duration of the x-ray pulses is about 1 fs to about 100 fs.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE SEVERAL VIEWS OF THE DRAWING(S)

The detailed description is described with reference to the accompanying figures. The use of the same reference numbers in different instances in the description and the figures may indicate similar or identical items.

FIG. 3A shows the betatron spectra for a 6 mm round jet and a 7 mm structured gas target measured using 6 pairs of balanced (Ross) transmission filters. An enhancement of the on-axis flux can be observed for the structured jet. Due to the finite size of the X-ray camera, only part of the whole beam was detected. FIG. 3B shows the spectral flux extracted for 3 Ross pairs. The error bars are due to counting statistics and the mismatch in the filter transmission. The pressure of the 6 mm jet was optimized for maximum emission. The number of photons were extracted at 5.25 keV to be for the 6 mm jet: $10 \times 10^8$ ph/0.1% b.w/sr. For a 100% b.w. and an angular divergence of 15 mrad (estimated from the electron beam divergence), the number of photons in the whole beam is 2×10⁸ photons/pulse. In case of the 7 mm jet, 17.5×10⁸ ph/0.1% b.w./sr lead to 4×10⁹ photons/pulse for a divergence of 50 mrad.

FIG. 4A and FIG. 4B show the results using a 5000 lines/mm Au transmission grating: FIG. 4B shows the extracted spectra. The spectrally integrated photon number for the 6 mm leads 0.5×10¹² photons/sr and for an estimated 15 mrad divergence to an estimated number of 1×10⁸ photons/pulse. For the 7 mm jet, 2×10¹² photons/sr and 5×10⁹ photons/pulse (assuming a 50 mrad divergence).

DETAILED DESCRIPTION

The following detailed description is exemplary in nature and is not intended to limit the invention or the application and uses of the invention. Furthermore, there is no intention to be bound by any expressed or implied theory presented in the following detailed description or the appended drawings.

Turning to the drawings, and as described in detail herein, embodiments of the disclosure provide methods, devices and systems useful to generate and control x-ray pulses via betatron emission of ultrashort relativistic electron bunches transversely oscillating in a plasma accelerator structure.

Figure 1:
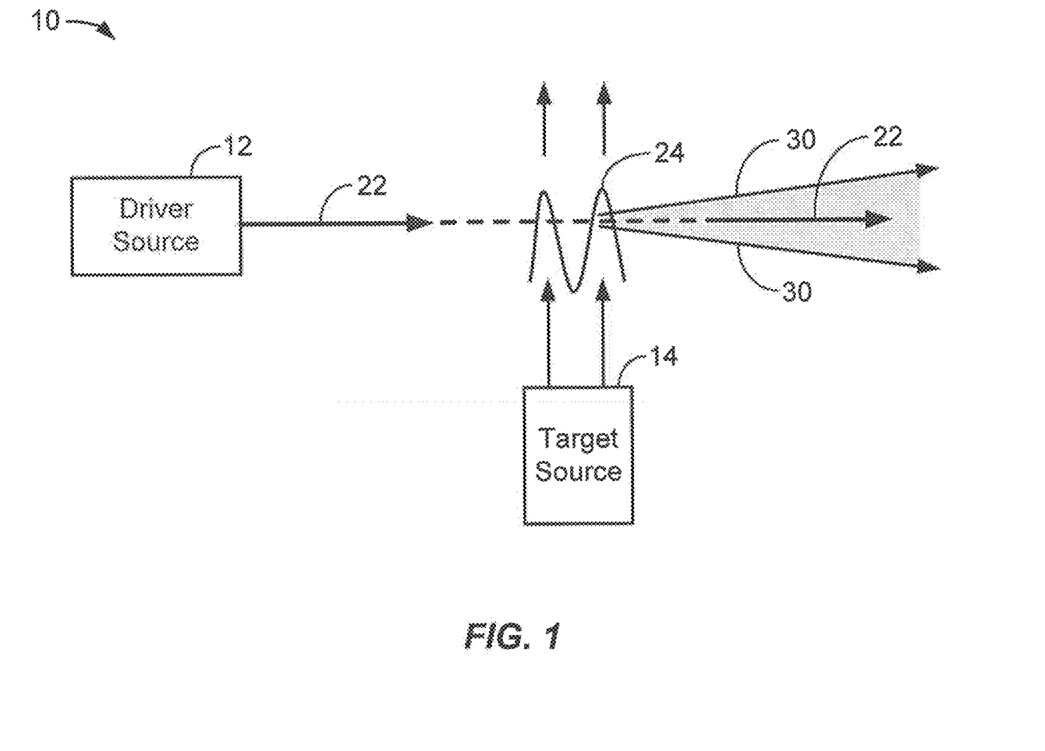
FIG. 1 shows a system for generating tunable x-ray pulses according to an embodiment.

FIG. 1 shows a tunable x-ray system 10 for generating tunable x-ray pulses according to an embodiment. The components of system 10 may be embodied in a single device, e.g., single device housing structure holding the various system components. As shown, tunable x-ray system 10 includes a driver source 12 that generates one or multiple driver pulses (also "driver"), and a target source 14 that emits the target material. The target source typically emits a plasma or gas as the target material that is then ionized by the driver, but in some cases the target material also may be ionized before the driver interacts with it, e.g., using an additional laser pulse. The target source 14 is configured and arranged so that the emitted target material intersects the propagation axis 22 of the driver pulse, and the target source 14 is configured so that the emitted target material has a tailored density profile 24 along the propagation axis 22 of the driver pulse. In some embodiments, the tailored density profile 24 may include more than two density peaks, each separated by a lower density region. For example, in one embodiment as shown, the tailored density profile 24 along the propagation axis 22 has a first density peak region followed by a lower density region followed by a second density peak region. Interaction of the driver pulse with the target material along the propagation axis acts as a plasma accelerator and results in betatron emissions 30 in an x-ray wavelength range as will be described in more detail herein. The betatron emissions 30 include x-ray pulses propagating along the propagation direction of the driver pulse with a narrow angular spread relative to the propagation axis 22. The first density peak and the second density peak each may have a higher density than the lower density region and the lengths of the peaks (i.e., interaction length of driver pulse with target material along propagation axis within each density peak) can be different. In an embodiment, the tailored density profile 24 has an "M" type shape (i.e., as shown wherein the propagation axis 22 intersects the left part or peak of the "M" and travels through middle section of the "M" and out of the right peak of the "M"). The target source 14 may include a nozzle including two exit apertures, or two separate nozzles, each with an exit aperture, or multiple nozzles, each with one or more exit apertures. The target material may include a plasma or ionized gas. The driver source may include a laser, e.g., a pulsed laser, an electron beam source, or other source capable of generating pulses having a controllable pulse length on the order of 1 to 5 femtosecond (fs) or less, to 50 fs or greater. The power of the driver source may be on the order of TW to PW per pulse. For example, the source could include a pulsed beam of ultrashort relativistic electron bunches. The source could also include a laser pulse that generates a plasma wave and an external electron beam that is injected into the plasma wave.

The plasma accelerator is driven by the driver pulse (also "driver"), such as an ultrashort high-power laser pulse or a relativistic electron bunch. The driver is focused into the target material (also "target") comprising atoms or ions, such as a gas target or a pre-ionized plasma target, along a driver propagation axis (also "propagation axis"). Upon entering the target the driver excites a plasma wave. Electrons in the target that interact with the front of the driver are transversely expelled through the ponderomotive (laser) or the electrostatic force (electron beam). For sufficiently high laser intensities or electron beam currents, all background plasma electrons are expelled and only positive ions, which are effectively stationary on the time scale of the driver pulse, remain in the region behind the driver. The initially transversely expelled electrons are attracted back toward the propagation axis through the electrostatic force of the positive ions. In combination with the quasi-stationary ions they form a positively charged cavity, named the "bubble," which trails the driver at its group velocity. Background plasma electrons are injected into the bubble through self-injection or external injection. For self-injection, returning electrons near the back of bubble that have a suitable momentum distribution are scattered into the bubble by the electrostatic potential generated by the plasma density perturbation of the wake created by the plasma wave ("plasma wake"). For external injection, electrons are injected through external support, e.g., using a second laser pulse, ionization from a different atomic species in a gas mixture or a plasma density gradient. In both cases, the injected electrons are subsequently accelerated to relativistic kinetic energies by the electrostatic potential of the plasma wave over an acceleration distance of only a few micrometers to centimeters (μm-cm). Since the electrons are injected with a non-zero transverse momentum, they perform transverse betatron oscillations during the acceleration process. The transverse oscillations of the electrons lead to X-ray emission via betatron radiation. For relativistic electron beams, the emission is concentrated into a narrow forward cone. The spectrum of the generated radiation includes harmonics of the fundamental photon energy given by:

$$\hbar\omega = \frac{2\gamma^2 hc}{\lambda_\beta} \frac{1}{(1+K^2/2)} \quad (1)$$

where γ is the electron energy normalized by the electron rest mass, $\lambda_\beta$ the period of the betatron oscillation and K is the deflection parameter. In the case of a plasma betatron source for an ideal fully evacuated bubble, the parameters can be approximated by the emission of an electron with a constant energy at the maximum accelerated energy by $\Delta_\beta = \sqrt{2\gamma}\lambda_\beta$, where the plasma wavelength is given by $\lambda_p = 2\pi c/\omega_p$ with $\omega_p = \sqrt{e^2 n_e/m_e \epsilon_0}$ and the plasma density $n_e$, the vacuum speed of light c, the elementary charge e, the electron rest mass $m_e$ and the electric permittivity of free space $\epsilon_0$. In practical units $\lambda_\beta[\mu m] = 4.7 \times 10^{10}\sqrt{\gamma/n_e[cm^{-3}]}$. In the bubble regime, the deflection parameter can be approximated as $K = r_\delta k_p \sqrt{\gamma/2}$ where $r_\delta$ is the amplitude of the oscillation, which in practical units can be written as $K = 1.3 \times 10^{-10} \sqrt{\gamma n_e[cm^{-3}]}\, r_\delta\,[\mu m]$. Depending on the amplitude of the oscillation, the spectrum can extend to very high harmonics. In particular, for K>>1, the emitted photon energy distribution resembles a wiggler radiation spectrum with many closely spaced harmonics of the wavelength as would be emitted by a purely sinusoidal trajectory. The spectrum may be characterized by a critical photon energy, above which the number of radiated photons starts to drop significantly. In the wiggler regime, the critical photon energy for plasma-driven betatron radiation in the bubble regime is given by:

$$\hbar\omega_{crit} = \frac{3}{2} K \gamma^2 \frac{hc}{\lambda_\beta} \simeq 10^{-23} \gamma^2 n_e[cm^{-3}] r_\beta[\mu m]. \text{ (in units of [keV])} \quad (2)$$

For plasma accelerators, the photon energy can be tuned over a large range. The number of emitted photons per electron and per betatron period scales in the wiggler regime (K>>1) as:

$$N_{ph} \approx 3 \times 10^{-2} K \approx 4 \times 10^{-12} \sqrt{\gamma n_e[cm^{-3}]} r_\beta[\mu m] \quad (3)$$

According to equations (2) and (3), the emitted number of photons, and their energy, may be increased by increasing the electron beam energy. However, this requires increasing the power of the driving laser pulse and longer plasma jets. However, $N_{ph}$ scales only weakly with the beam energy as $\partial \gamma^{1/4}$ (since $r_\delta \partial \gamma^{-1/4}$). Increasing the laser power or the plasma length is often not possible and higher power lasers typically have a reduced repetition rate and increased size and cost. Increasing $N_{ph}$ by increasing the plasma density is limited because the driver pulse becomes mismatched with the plasma. Here, a method is described that manipulates the betatron oscillation amplitude $r_\beta$ to control and enhance the number of emitted photons and their spectrum.

Figure 2:
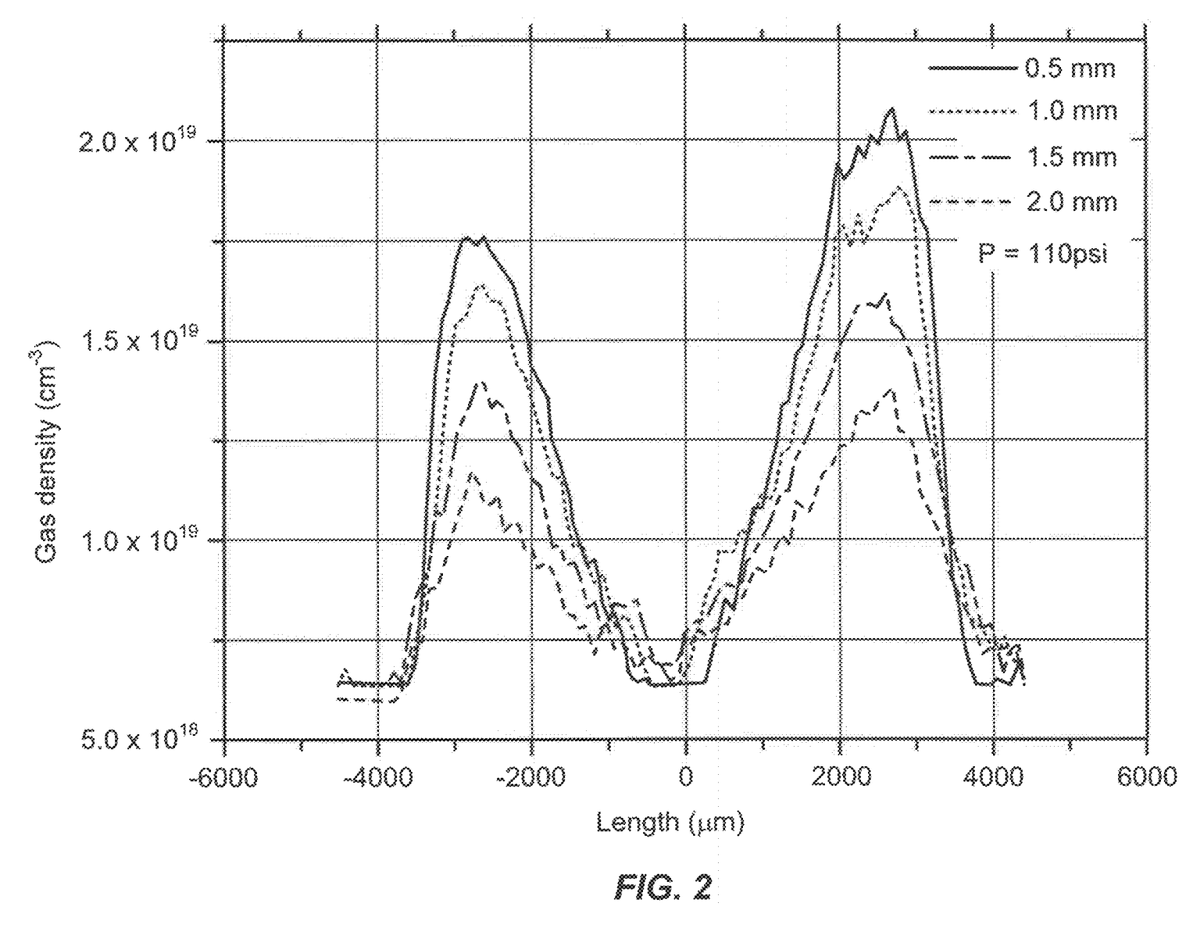
FIG. 2 shows a density profile of a target gas according to an embodiment.

According to an embodiment, a specifically tailored plasma density profile is used to increase and control the electron betatron oscillation amplitude and thus the X-ray properties. In an embodiment, the plasma density profile includes two or more peaks interrupted by one or more low-density region(s). For example, in a specific embodiment, a double-peaked "M"-shaped density profile is used as shown in FIG. 2. The Length axis of FIG. 2 also represents the direction of interaction of the driver with the gas target, i.e., the driver interacts with the left peak, then the region of lower gas density then the right peak (hence the "M" shaped density structure or profile). The multi-peaked density structure enables control of the electron and x-ray beam properties and increases the stability of the x-ray source. More specifically, the first density peak acts as electron injector and linear accelerator, the subsequent density peak(s) as x-ray radiators and electron energy boosters. The dedicated electron injector enables a stable and reproducible operation of the X-ray source. The X-ray and electron beam properties are controlled by variation of the density peak profiles, in particular the lengths of the peaks, peak densities and density contrasts.

Previous theoretical work by Ta Phuoc et. al [Ta Phuoc, K. et al. Betatron radiation from density tailored plasmas. *Phys. Plasmas* 15, (2008).; hereinafter "Ta Phuoc"] proposed interaction of a high-power laser with a plasma profile that has a density depression. The laser drives a bubble and electrons are injected and accelerated; in the density depression, the longitudinal accelerating and the transverse focusing fields are essentially absent due to their linear dependence on the plasma density $n_e$. As a result, an electron bunch generated in the first peak undergoes effectively ballistic propagation and transversally expands due to its finite emittance. As the driver enters the plasma density after the depression, the driver starts to drive a bubble again and electrons that are located off-axis are subject to the transverse restoring force. Because of the increased transverse size of the electron bunch, the electrons perform large-amplitude betatron oscillations, which leads to a significant increase in the number of emitted photons and the critical photon energy of the generated spectrum. The amplitude of the oscillation can be controlled by the plasma density profile and the laser parameters.

In a preliminary experimental study, it has been demonstrated that the present methodology can significantly enhance the betatron emission relative to Ta Phuoc. In the experimental study a significantly different gas density profile compared to that of Ta Phuoc was used. In particular, Ta Phuoc proposed a short width of the density depression of 120 µm, whereas in the experiment a distance of about 2.2 mm has been used to demonstrate a significant enhancement. Note that Ta Phuoc even predicts a significant decrease in the X-ray flux compared to a flat density for a long depression. The density profile of the present embodiment has a double-peaked "M"-shaped structure (see FIG. 2), whereas Ta Phuoc assumes a flat density profile interrupted by a depression. Furthermore, whereas in Ta Phuoc the laser evolution is not considered, it was found that the diffraction of the driver in the depression is important for a significant enhancement in the X-ray radiation. In particular, diffraction of the driver is important to using a longer density depression, which allows for larger transverse betatron amplitude. Only by taking into account an increased laser spot size due to diffraction during the density depression is it possible to increase the transverse dimension of the accelerating plasma wake after the depression. This is important for the efficient re-capture of the expanding electron beam after the density depression. Furthermore, it allows an operation in a more linear regime. As the amplitudes of the oscillations after the depression are essentially given by the transverse offset of the electrons after the quasi-free drift, this leads to significantly increased betatron amplitudes and thus enhancement in the X-ray beam properties, including the photon energy and the number of emitted photons. Furthermore, the adjustment of the plasma profiles and distance between the driver and the two (or more) jets also allows for control of the betatron oscillation amplitude and consequently the x-ray beam parameters. Note that Ta Phuoc does not contemplate using the maximum density of the peak and its length as a means to control and enhance the X-ray parameters. Furthermore, Ta Phuoc assumes that after the density depression, the accelerator still operates in the bubble regime. However, after a longer depression and laser diffraction, as in the present embodiments, the laser intensity can be sufficiently low that it operates in a more linear plasma wave regime. The nonlinear transverse fields in this case can lead to additional enhancement of X-ray emission. The regime in which the accelerator operates after the first density depression can be mainly controlled by the length of the depression and the density profile of the first and the second peak.

In plasma accelerators, the maximum electron energy is limited to the acceleration over the dephasing length, when the electrons outrun the accelerating phase of the cavity. The significantly larger betatron amplitude in case of the structured density profile of the present embodiments leads to an effective lower axial electron velocity. This implies that the dephasing length is increased and the X-ray emission further enhanced using the same laser parameters, as well as the electron energy can be increased.

Figure 3A:
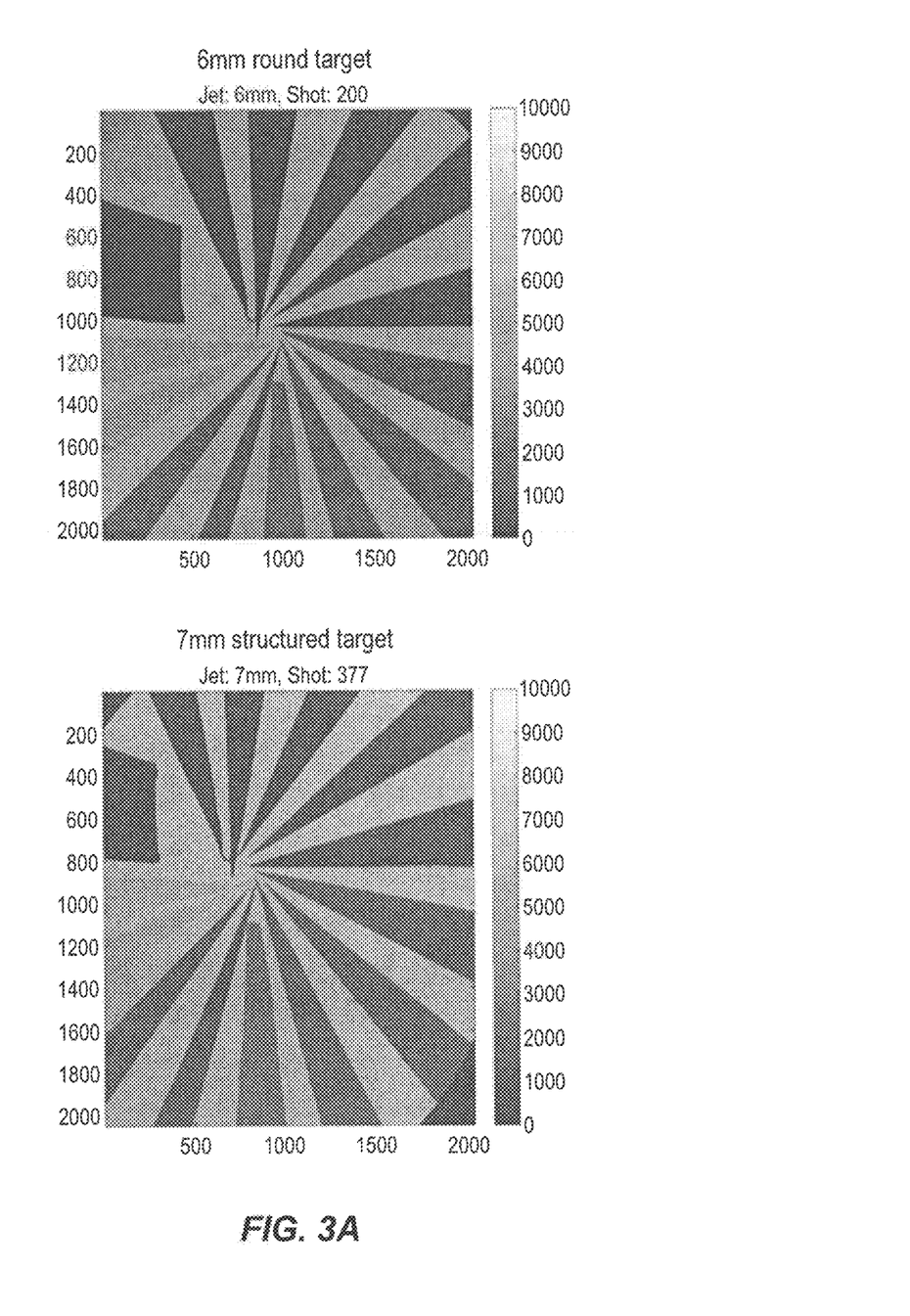
FIG. 3A and FIG. 3B show results of an embodiment based on balanced transmission (Ross) filter pair measurements.
Figure 3B:
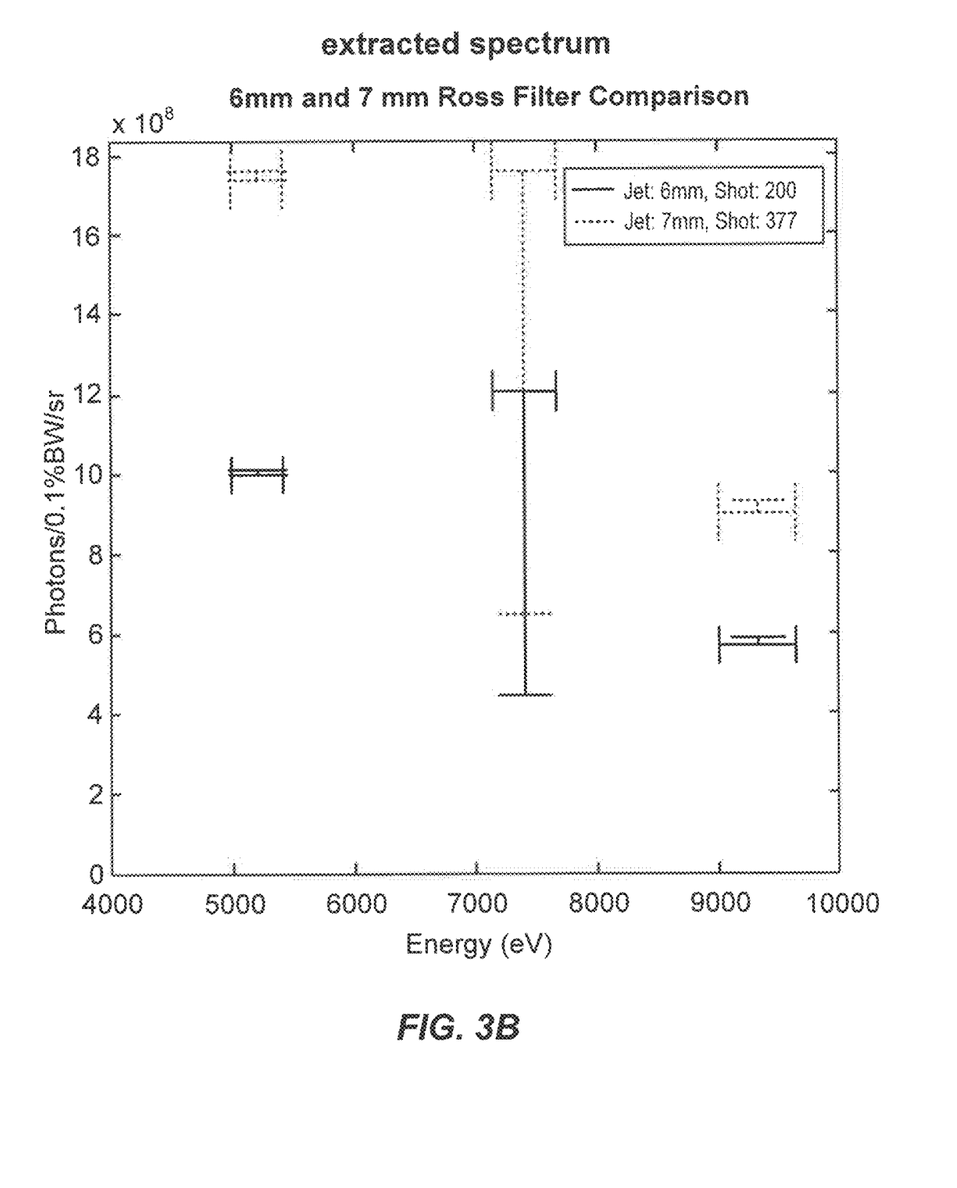
Figure 4A:
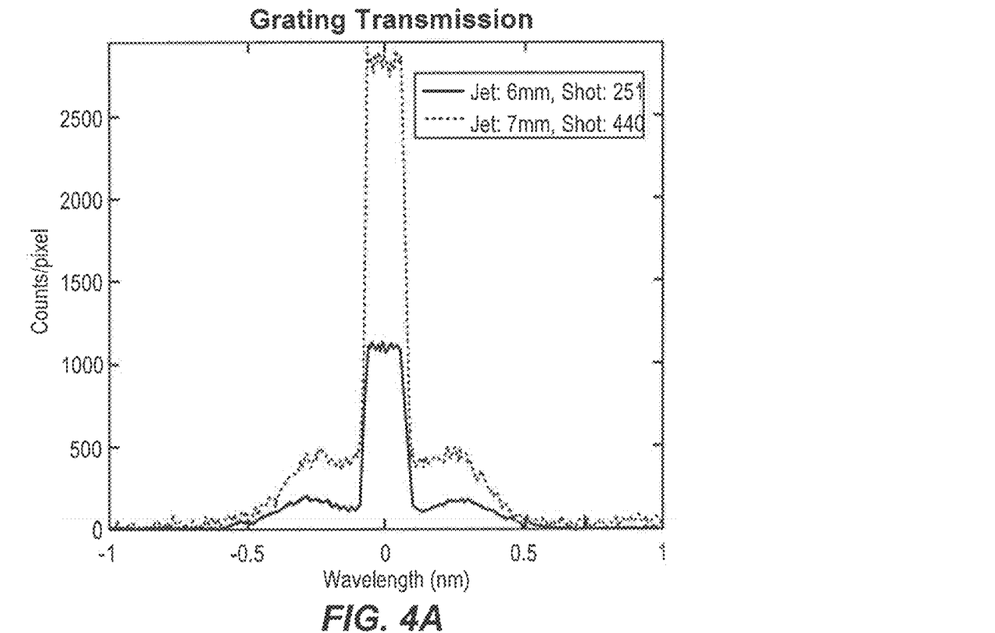
FIG. 4A shows the transmitted radiation through a 5000 lines/mm grating for a 6 mm round jet and a 7 mm structured jet.
Figure 4B:
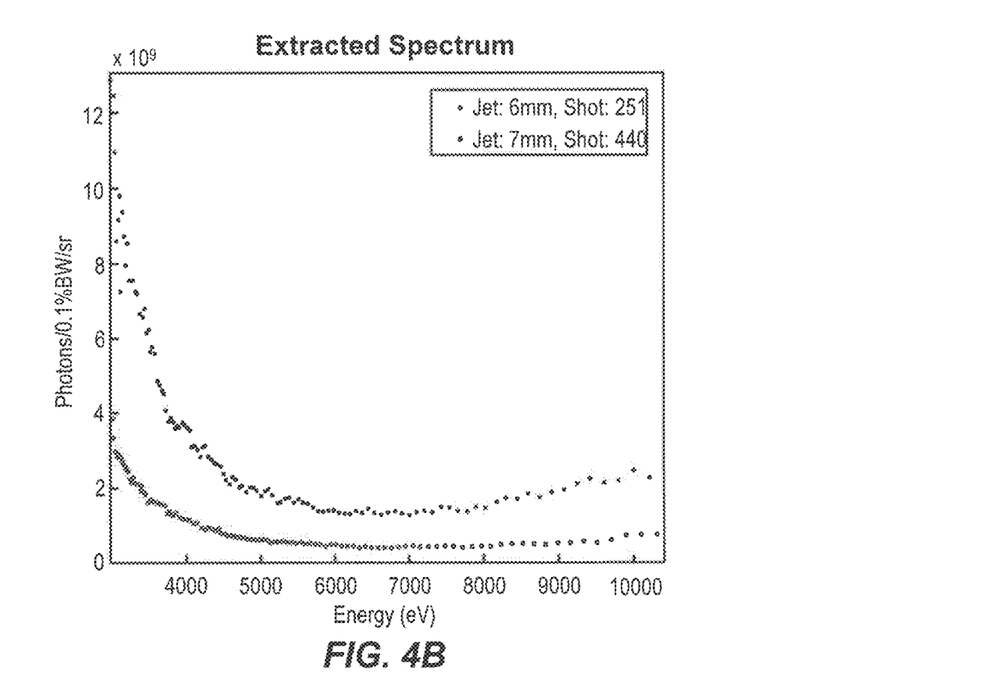
Figure 5:
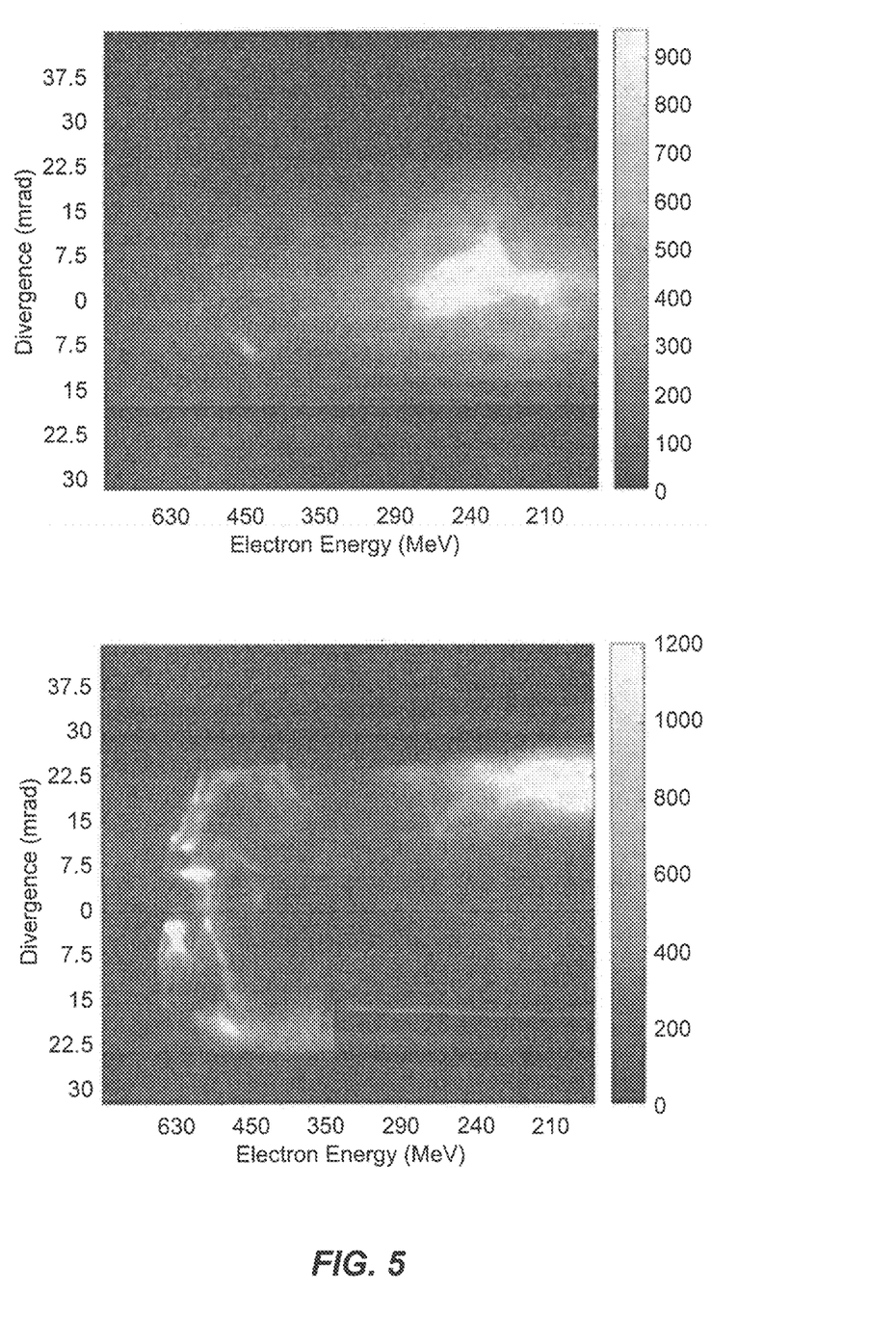
FIG. 5 shows angularly resolved electron beam spectra, according to an embodiment.

An experiment to demonstrate the effect was performed. In the experiment, the radiation generated from a structured double-peaked "M"-shaped density profile was compared to non-structured, round 4 and 6 mm diameter gas jets with a radial Gaussian density profile. At an interaction height of 0.5 mm above the gas jet nozzle, the density peaks of the tailored gas jet each have a width of about 2.2 mm and are interrupted by a density depression of about 2.3 mm as can be seen in the specific example shown in FIG. 2. Because the 6 mm round jet generated significantly brighter X-rays than the 4 mm jet, the 6 mm jet was mainly compared to the tailored jet. Multiple methods of spectrally characterizing the X-ray beam were used. The results based on balanced transmission (Ross) filter pair measurements are shown in FIG. 3A and FIG. 3B, and in FIG. 4A and FIG. 4B the results using a 5000 lines/mm Au transmission grating are shown. It can be clearly seen that both the number of emitted photons and the critical energy of the betatron radiation are significantly enhanced using the tailored gas density profile. Angularly resolved electron beam spectra (see FIG. 5) were also simultaneously observed. In comparison to the round jet, the electron beams generated by the tailored density profile have a significantly larger divergence, which supports the model described above as the reason for the X-ray enhancement. Note that due to a finite detector size, only part of the emitted betatron radiation was observed. From the observed electron beams, an estimate of the emission angle of the X-ray pulse can be obtained and from that the total number of photons in the entire X-ray beam can be obtained. Since the observed electron beam divergence of the double-peaked jet is clipped by the aperture of the dipole magnet, a conservative low value of 50 mrad was used. The observed number of photons using the transmission grating agree well with the Ross filter pair measurement. In case of the 6 mm non-structured jet, $\sim 1 \times 10^8$ photons/pulse was observed using the grating and $\sim 2 \times 10^8$ photons/pulse was observed using the filters. For the density-tailored jet, $5 \times 10^9$ photons/pulse were observed with the grating and $4 \times 10^9$ photons/pulse were observed with the filters. Note that for the structured jet, not only is the total number of photons increased but also the on-axis flux. With the same laser parameters, the radiation generated by the jet with the density depression was also significantly more reproducible because of the separate (integrated) injector and accelerator stage of the structured jet.

Figure 6:
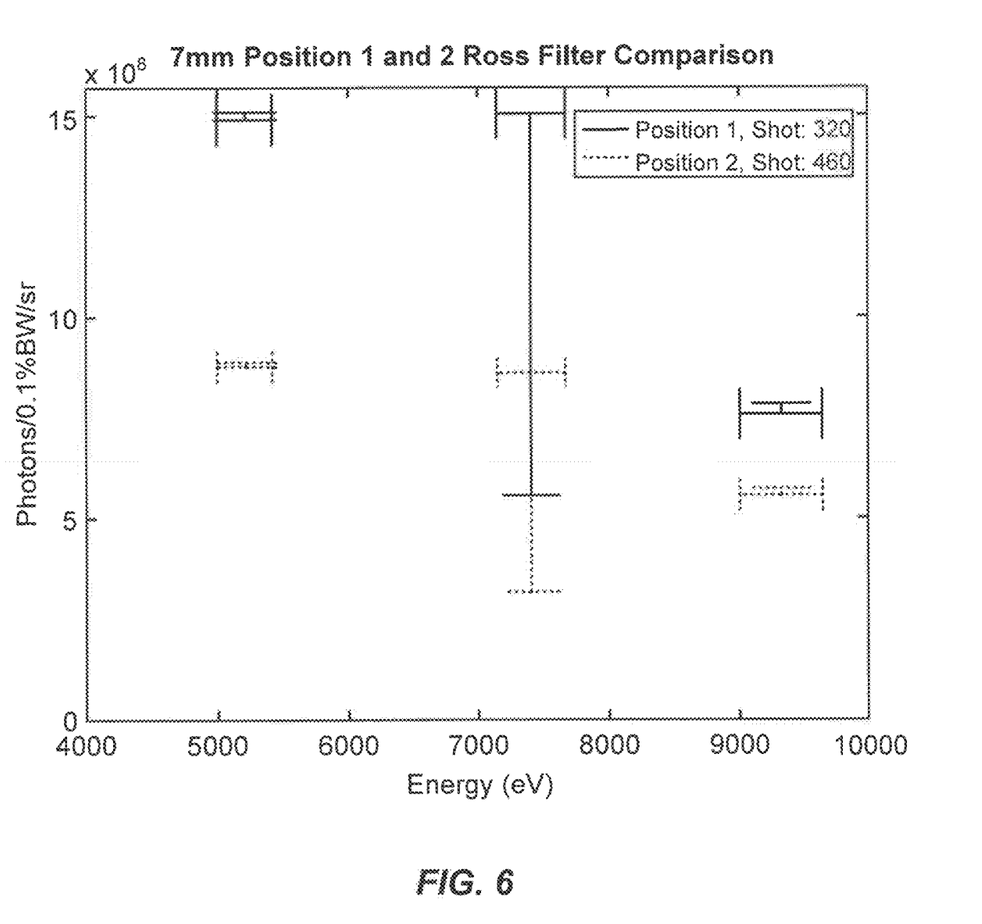
FIG. 6 shows a graph exhibiting an ability to control x-ray emissions through adjustment of the length of the density depression region of the tailored density profile according to an embodiment.

Control of the X-ray parameters was demonstrated through varying the profile of the density depression. To this end, the distance from the gas nozzle exit to the interaction point of the driver (e.g., laser) with the gas was increased. Because the gas jet diverges, this leads to a narrower density depression, a smaller contrast between the density peak and trough and less sharp edges of the density profile (see FIG. 2). In order to compare the results with previous measurements, the backing pressure was increased to compensate for the lower gas density higher above the nozzle exit. In particular, FIG. 6 shows the decrease in X-ray flux after increasing the distance from the nozzle to the interaction point from 0.5 mm to 1.5 mm. This can be explained by a betatron oscillation amplitude in this case caused by an effectively shorter density depression and a smaller peak-to-valley contrast in density, both of which lead to a smaller electron beam size at the entrance of the second density peak.

The x-ray source systems provided herein are advantageously small or compact in scale relative to larger laboratory systems. For example, x-ray source systems according to various embodiments may have a structural size (e.g., combined driver source, target source and driver to target distance) having dimensions on the order of few meters or greater.

U.S. Provisional Patent Application Ser. No. 62/728,324, which is incorporated by reference herein, includes an Appendix A, which discloses additional aspects and features of tunable x-ray source methods and systems.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A tunable ultrafast x-ray source, comprising:
a driver configured to generate a driver pulse;
a target source configured to emit a target material having a tailored density profile along a propagation axis of the driver pulse, the tailored density profile along the propagation axis having a first density peak region followed by a lower density region followed by a second density peak region,
wherein interaction of the driver pulse with the target material along the propagation axis results in betatron emissions in an x-ray wavelength range.

2. The tunable x-ray source of claim 1, wherein the driver comprises a laser source.

3. The tunable x-ray source of claim 2, wherein the laser source is configured to generate laser pulses having a controllable pulse duration of about 1 fs to about 50 fs.

4. The tunable x-ray source of claim 3, wherein each pulse has a power of from about 0.1 MW to about 1 MW and a pulse duration of about 1 fs to about 100 fs.

5. The tunable x-ray source of claim 1, wherein the target material comprises a plasma.

6. A method of generating tunable x-ray emissions, the method comprising:
generating a driver pulse that propagates along a propagation axis;
generating a target, the ionized target having a tailored density profile along the propagation axis, the tailored density profile along the propagation axis having a first density peak followed by a lower density region followed by a second density peak, wherein interaction of the driver pulse with the target results in betatron emissions in an x-ray wavelength range.

7. The method of claim 6, wherein the driver pulse includes a laser pulse having a pulse duration of about 1 fs to about 50 fs.

8. The method of claim 6, wherein the driver pulse has a power of from about 1 TW to about 1 PW or more or from about 100 A to about 10 kA or more.

9. The method of claim 6, wherein the target material comprises a plasma.

10. The method of claim 6, wherein the betatron emissions has an energy of from about 0.5 keV to about 100 keV.

11. The method of claim 6, wherein the generating a driver pulse includes generating a plurality of driver pulses, wherein each of the plurality of driver pulses has a power of from about 0.1 MW to about 1 MW and a pulse duration of from about 1 fs to about 100 fs.

12. A method of generating tunable x-ray emissions, the method comprising:
generating a laser pulse that propagates along a propagation axis;
generating a target, the ionized target comprising a plasma having a tailored density profile along the propagation axis, the tailored density profile along the propagation axis having a first density peak followed by a lower density region followed by a second density peak, wherein interaction of the driver pulse with the target results in betatron emissions in an x-ray wavelength range.

13. The method of claim 12, wherein the laser pulse has a pulse duration of about 1 fs to about 100 fs.

14. The method of claim 12, wherein the betatron emissions has an energy of from about 0.5 keV to about 100 keV.

15. The method of claim 12, wherein the laser pulse has a power of from about 0.1 MW to about 1 MW.

16. The method of claim 12, wherein the generating a laser pulse includes generating a plurality of laser pulses, wherein each of the plurality of laser pulses has a power of from about 0.1 MW to about 1 MW and a pulse duration of from about 1 fs to about 100 fs.

* * * * *